(12) United States Patent
Cavallaro et al.

(10) Patent No.: US 6,828,720 B2
(45) Date of Patent: Dec. 7, 2004

(54) COMPACT FLUORESCENT SUN-TANNING LAMP

(75) Inventors: Albert Cavallaro, Florida, NY (US); Steven C. Farley, Montgomery, NY (US)

(73) Assignee: Osram Sylvania Inc., Danvers, MA (US)

( * ) Notice: Subject to any disclaimer, the term of this patent is extended or adjusted under 35 U.S.C. 154(b) by 21 days.

(21) Appl. No.: 10/323,379

(22) Filed: Dec. 18, 2002

(65) Prior Publication Data

US 2004/0119395 A1 Jun. 24, 2004

(51) Int. Cl.$^7$ .............................. H01K 1/26; F21V 14/00
(52) U.S. Cl. ...................... 313/489; 313/110; 313/112; 313/117; 313/493; 313/634; 362/255; 362/311
(58) Field of Search ................................. 313/110, 112, 313/117, 493, 573, 634; 362/255, 291, 296, 311

(56) References Cited

U.S. PATENT DOCUMENTS

| | | | |
|---|---|---|---|
| 3,988,628 A | * 10/1976 | Clausen ...................... 313/112 |
| 4,288,713 A | 9/1981 | Marlor ........................ 131/117 |
| 4,527,083 A | * 7/1985 | Op De Beeck et al. .... 313/573 |
| 5,635,794 A | 6/1997 | Koerfer ....................... 313/493 |
| 2002/0024278 A1 | * 2/2002 | Matsuda et al. ............. 313/112 |

* cited by examiner

Primary Examiner—Nemeshkumar D. Patel
Assistant Examiner—Sharlene Leurig
(74) Attorney, Agent, or Firm—Carlo S. Bessone

(57) ABSTRACT

A U-shaped compact fluorescent sun-tanning lamp (10) capable of generating and transmitting desired and undesired wavelengths of ultraviolet radiation, for example, the desired wavelength is in the range of 352 nm and the undesired wavelength is in the range of 254 nm. The lamp (10) comprises two lamp tubes (12) that are transparent to the desired wavelength of the ultraviolet radiation and substantially opaque to the undesired wavelength of the ultraviolet radiation. The tubes (12) are connected at the upper portion by a bight (14) that in an unmodified state is transparent to both the desired and the undesired wavelengths of the ultraviolet radiation. A modification (16) on the bight (14) is opaque to at least the undesired wavelength of ultraviolet radiation. In a preferred embodiment the modification is a ceramic paint (18).

6 Claims, 1 Drawing Sheet

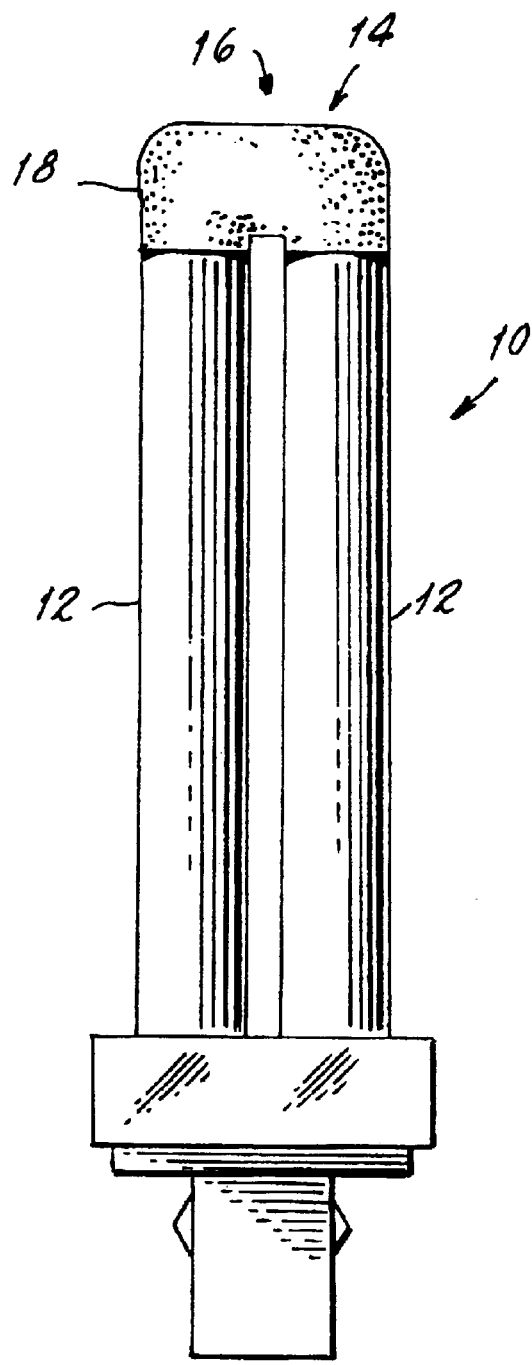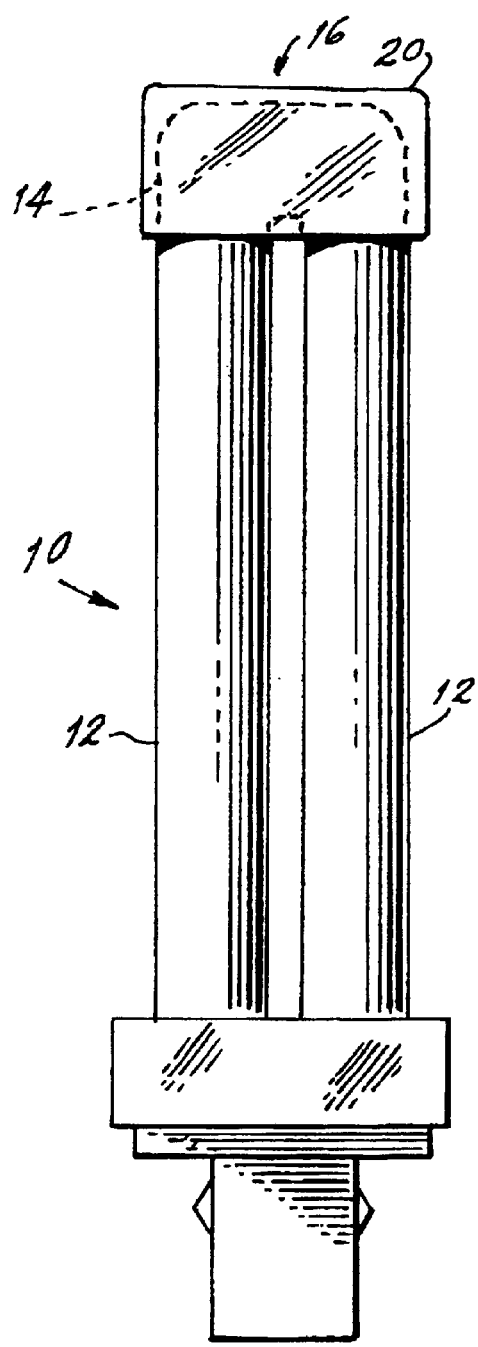

COMPACT FLUORESCENT SUN-TANNING LAMP

TECHNICAL FIELD

This invention relates to compact fluorescent lamps and more particularly to compact fluorescent lamps to be used for sun tanning.

BACKGROUND ART

Sun tanning booths normally employ linear fluorescent lamps interiorly coated with a phosphor that emits in the ultraviolet or tanning portion of the spectrum. The phosphors used emit radiation in both a desirable range, i.e., 352 nm, and an undesirable range, i.e., 254 nm. The latter range, which is also known as UV-C emission, is considered to be harmful and the FDA regulates its amount, relative to UV-B emission. In the conventional linear fluorescent lamps usually employed, the soda-lime glass from which the lamp envelopes are made absorbs the undesirable 254 nm radiation. However, when compact fluorescent lamps are prepared from the same soda-lime glass and using the same phosphors, it is found that impermissible amounts of the undesired 254 nm radiation are emitted.

It would be an advance in the art if compact fluorescent lamps could be employed, not only in sun tanning booths, but also in certain medical applications where the application of 352 nm radiation is desirable.

DISCLOSURE OF INVENTION

It is, therefore, an object of the invention to obviate the disadvantages of the prior art.

It is another object of the invention to enhance the use of compact fluorescent lamps.

It is yet another object of the invention to reduce or eliminate the emission of 254 nm radiation from compact fluorescent UV emitting lamps.

These objects are accomplished, in one aspect of the invention, by the provision of a U-shaped compact fluorescent lamp comprising two lamp tubes transparent to a desired wavelength of ultraviolet radiation connected by a bight transparent to the desired wavelength and an undesired wavelength with a modification on the bight opaque to at least the undesired wavelength.

It has been discovered that the unwanted or undesirable radiation emanating from compact fluorescent UV lamps comes from the bight of the lamp. Since both the soda-lime glass and the phosphor are normally good absorbers of 254 nm radiation, provided that the thickness is great enough, it is apparent that it is the manufacturing process that causes the undesired emission. Apparently, this is caused by the fact that during manufacture of the lamps the thickness of the glass in the area of the bight is thinned. Also, the phosphor applied to the area of the bight is less than the thickness of the phosphor on the linear tubes of the lamp. These thinner areas allow the undesired emission of the 254 nm radiation. By applying a modification to the bight that is opaque to the 254 nm radiation, the problem is solved and the convenience of the compact fluorescent lamp is available for both sun tanning and medical operations.

BRIEF DESCRIPTION OF THE DRAWINGS

FIG. 1 is an elevational view of an embodiment of the invention; and

FIG. 2 is an elevational view of an alternate embodiment of the invention.

BEST MODE FOR CARRYING OUT THE INVENTION

For a better understanding of the present invention, together with other and further objects, advantages and capabilities thereof, reference is made to the following disclosure and appended claims in conjunction with the above-described drawings.

Referring now to the drawings with greater particularity, there is shown in FIG. 1 a U-shaped compact fluorescent sun-tanning lamp 10 capable of generating and transmitting desired and undesired wavelengths of ultraviolet radiation. In this particular embodiment the desired wavelength is in the range of 352 nm and the undesired wavelength is in the range of 254 nm. The lamp 10 comprises two lamp tubes 12 that are transparent to the desired wavelength of the ultraviolet radiation and substantially opaque to the undesired wavelength of the ultraviolet radiation. The tubes 12 are connected at the upper portion by a bight 14 that in an unmodified state is transparent to both the desired and the undesired wavelengths of the ultraviolet radiation. As noted, it has been discovered that the undesired radiation emanates from the bight 14 because of the manufacturing process, whereby the normal absorbing effect of the soda-lime glass and phosphor have been compromised by the thinning of the materials. Although not shown, it is possible for lamp 12 to contain more than two lamp tubes 12.

By providing a modification 16 on the bight 14 that is opaque to at least the undesired wavelength of ultraviolet radiation the problem is eliminated.

In the preferred embodiment of the invention shown in FIG. 1, the modification 16 comprises a ceramic paint 18. Such a paint can be, for example, Aremco C4040, available from Aremco Products, Inc., Valley cottage, N.Y. The paint contains a high percentage (i.e., a solid content by weight of approximately 45%) of titanium dioxide. Other heavy metal oxides may be equally suitable.

Alternatively, a molded cap 20, as shown in FIG. 2 can be used. A low cost PVC material can be used for the cap 20, as well as any other material that either is opaque to UV-C radiation or that can be rendered opaque to such radiation. If a cap is used it should be cemented to the lamp so that it cannot easily be removed.

While there have been shown and described what are at present considered to be the preferred embodiments of the invention, it will be apparent to those skilled in the art that various changes and modification can be made herein without departing from the scope of the invention as defined by the appended claims.

What is claimed is:

1. A U-shaped compact fluorescent lamp comprising:
   two lamp tubes transparent to a desired wavelength of ultraviolet radiation comprising a wavelength peak of 352 nm connected by a bight transparent to said desired wavelength and an undesired wavelength comprising a wavelength peak of 254 nm; and
   a modification only on said bight opaque to at least said undesired wavelengths.

2. The compact fluorescent lamp of claim 1 wherein said modification comprises a ceramic paint.

3. The compact fluorescent lamp of claim 1 wherein said modification comprises a molded cap.

4. A U-shaped compact fluorescent sun-tanning lamp capable of generating and transmitting desired wavelengths of ultraviolet radiation including a wavelength peak of 352 nm and undesired wavelengths of ultraviolet radiation including a wavelength peak of 254 nm, said lamp comprising:

two lamp tubes transparent to said desired wavelength of said ultraviolet radiation and substantially opaque to said undesired wavelength of said ultraviolet radiation connected by a bight that in an unmodified state is transparent to both said desired and said undesired wavelengths of said ultraviolet radiation; and a modification only on said bight preventing transmission of at least said undesired wavelength of said ultraviolet radiation.

5. The compact fluorescent lamp of claim 4 wherein said modification comprises a ceramic paint.

6. The compact fluorescent lamp of claim 4 wherein said modification comprises a molded cap.

* * * * *